United States Patent [19]

Watanabe et al.

[11] Patent Number: 5,751,837
[45] Date of Patent: May 12, 1998

[54] X-RAY CT SCANNER SYSTEM HAVING A PLURALITY OF X-RAY SCANNER APPARATUS

[75] Inventors: Naofumi Watanabe, Tochigi-Ken; Shigeru Tanaka, Otawara, both of Japan

[73] Assignee: Kabushiki Kaisha Toshiba, Kawasaki, Japan

[21] Appl. No.: 683,910

[22] Filed: Jul. 19, 1996

Related U.S. Application Data

[63] Continuation of Ser. No. 216,868, Mar. 24, 1994, abandoned.

[30] Foreign Application Priority Data

Mar. 25, 1993 [JP] Japan ................... 5-065858

[51] Int. Cl.$^6$ .................................................. G06K 7/00
[52] U.S. Cl. ...................... 382/131; 378/165; 364/413.14
[58] Field of Search ..................... 382/305, 131; 378/165, 166, 162; 364/413.14, 413.15, 413.19

[56] References Cited

U.S. PATENT DOCUMENTS

| | | | |
|---|---|---|---|
| 4,630,202 | 12/1986 | Mori | 364/414 |
| 4,707,786 | 11/1987 | Dehner | 382/131 |
| 4,739,480 | 4/1988 | Oono et al. | 364/414 |
| 4,960,993 | 10/1990 | Shigyo | 250/327.2 |
| 4,982,415 | 1/1991 | Shibata et al. | 378/15 |
| 4,993,025 | 2/1991 | Vesel et al. | 370/94.1 |
| 5,111,044 | 5/1992 | Agano | 358/453 |
| 5,321,520 | 6/1994 | Inga et al. | 358/428 |
| 5,336,897 | 8/1994 | Watanabe et al. | 250/551 |

OTHER PUBLICATIONS

*Toshiba Review;* "Whole Body X-ray CT Scanner, Xforce"; T. Matsubayashi; 1991 vol. 46, No. 2, pp. 89–92.

K. Kimura et al., "Basic Principles and Clinical Applications of Helical Scan", pp. 110–120 (1993).

*Primary Examiner*—Jose L. Couso
*Assistant Examiner*—Matthew C. Bella
*Attorney, Agent, or Firm*—Finnegan, Henderson, Farabow, Garrett & Dunner, L.L.P.

[57] ABSTRACT

According to the present invention, there is provided an image data detecting apparatus for X-ray CT comprising a scanning apparatus including an X-ray tube for emitting X-rays while rotating about a patient, a detector for detecting X rays emitted by the X-ray tube and passing through the patient, and a memory unit for storing transmission X-ray data detected by the detector, and a transmitting/receiving unit for transmitting the transmission X-ray data stored in the memory unit together with an identification number for identifying the image data detecting apparatus. The image data detecting apparatus of the present invention can be set solely in an inspection site, thereby making it possible to save the space for inspection.

5 Claims, 7 Drawing Sheets

X-RAY CT SCANNER SYSTEM HAVING A PLURALITY OF X-RAY SCANNER APPARATUS

This is a continuation of application Ser. No. 08/216,868 filed Mar. 24, 1994, now abandoned.

BACKGROUND OF THE INVENTION

The present invention relates to a medical inspection system such as X-ray diagnostic apparatus, MRI (Magnetic Resonance Imaging) apparatus, SPECT (Single Photon Emission Computed Tomography) apparatus, etc.

So far, there has been known a medical inspection system such as X-ray diagnostic apparatus, MRI apparatus, SPECT apparatus, etc. Such a medical inspection system comprises a plurality of units, such as a scanner body (gantry), a couch, a high-voltage (HV) generator, a console, an imager, etc., designed and manufactured under the precondition that all of these units be disposed adjacent to each other.

Table 1 shows examples of the size of each unit constituting an X-ray CT (Computed Tomography) scanner.

TABLE 1

|  | width (mm) | depth (mm) | height (mm) |
| --- | --- | --- | --- |
| gantry | 2200 | 1000 | 1400 |
| couch | 700 | 2300 | 300 |
| HV generator | 600 | 400 | 250 |
| console | 1300 | 900 | 250 |
| imager | 600 | 800 | 150 |

Each of such units will be explained in detail, taking an X-ray CT scanner as an example.

FIG. 1 is a schematic illustration of a conventional X-ray CT scanner. A gantry 101 is provided with an X-ray tube 105, a detector 106 and a data acquisition system (DAS) 107. An image processing part 102 is equipped with a central processing unit (CPU) 109, an image reconstruction unit 110, an image processor 111 and a memory unit 112. A high-voltage generator 103 generates high voltage supplied to the X-ray tube 105. A couch 104 moves having a patient M thereon. The detector 106 detects X rays passing through the patient M and outputs an X-ray detection signal. The DAS 107 converts the X-ray detection signal to a digital signal. A console 108 includes an operation panel to perform various kinds of operation for the X-ray CT apparatus. The CPU 109 generates control signals to control these units. The image reconstruction unit 110 reconstructs an image from projection data detected by the detector 106. The image processor 111 performs image processings such as the enlarging, reducing, and transferring of the image reconstructed by the image reconstruction unit 110. The memory unit 112 stores three kinds of data which are the projection data transmitted from the DAS 107, the image reconstructed by the image reconstruction unit 110 or the image processed by the image processor 111. A display unit 113 displays an image signal transmitted via the image processor 111. An imager 114 prints to a film an image sent with the image signal.

With such a conventional X-ray CT scanner, however it has been impossible to work each of the units solely since all of the gantry 101, the image reconstruction unit 110 and the image processor 111 were controlled by the single CPU 109.

Namely, as aforementioned, the conventional medical inspection system has been designed under the precondition that each of the units constituting the system be arranged adjacent to or near to each other and the CPU set within the image processing part 102 control each of the other units. For that reason, even when measuring X-ray projection data, a pair of the gantry and the image processor always has to be together, thereby requiring a considerable space. Thus, no compact inspection system has been achieved yet.

SUMMARY OF THE INVENTION

Accordingly, it is an object of the present invention to provide a medical inspection system requiring little space for setting units required to detect data.

It is another object of the present invention to provide an image data detecting apparatus and an image processing apparatus being parts of a medical inspection system which both are capable of being arranged physically or spatially separate, thereby saving space for setting such an image data detecting apparatus.

It is still another object of the present invention to provide an image data detecting apparatus and an image processing apparatus being parts of a medical inspection system which both are capable of being arranged physically or spatially separate, thereby making it possible to process with only one image processing apparatus the detection data from a plurality of the image data detecting apparatus and enhancing wide use of such image processing apparatus.

It is further object of the present invention to provide an X-ray CT system capable of reducing the setting space for its units to detect data.

These and other objects can be achieved according to the present invention, in one aspect by providing an image data detecting apparatus comprising: a data collecting means including a data acquisition means for acquiring a medical data from an object under test and a memory means storing the data acquired by the data acquisition means; and an information transmitting means for transmitting the data stored in the memory means together with an identification code for identifying the data collecting means.

As another aspect, there is provided an image processing apparatus comprising: an inputting means for inputting an image data transmitted from an image data detecting means via an outer information transmitting means and an identification code for identifying the image data inputted through the inputting means with making reference to the identification code; an image reconstruction means for reconstructing a tomography based on the image data stored in the first memory means; and a second memory means for storing the tomography reconstructed by the image reconstruction means.

Further, as another aspect, there is provided a medical inspection system comprising: a data collecting means including a data acquisition means for acquiring a medical data from an object under test and a memory means storing the data acquired by the data acquisition means; an information transmitting means for transmitting the data stored in the memory means together with an identification code for identifying the data collecting means; and an image processing means separate from the data collecting means for inputting information transmitted by the information transmitting means, the image processing means comprising: an inputting means for inputting the image data transmitted by the information transmitting means and the identification code; a first memory means for storing the data inputted through the inputting means with making reference to the identification code; an image reconstruction means for reconstructing a tomography based on the image data stored in the first memory means; and a second memory means for storing the tomography reconstructed by the image reconstruction means with making reference to the identification code.

It is preferred that the image data detecting apparatus is applied to an X-ray computed tomography (CT) system or an X-ray diagnostic apparatus using an image intensifier.

It is also preferred that the information transmitting means includes means using an electric wave, a telephone circuit means, and a portable record medium.

DESCRIPTION OF THE PREFERRED EMBODIMENTS

The examples of the present invention will be explained hereinafter with reference to the accompanying drawings. An X-ray CT system and X-ray diagnostic system will be taken as a medical inspection system of the present invention.

Figure 1:
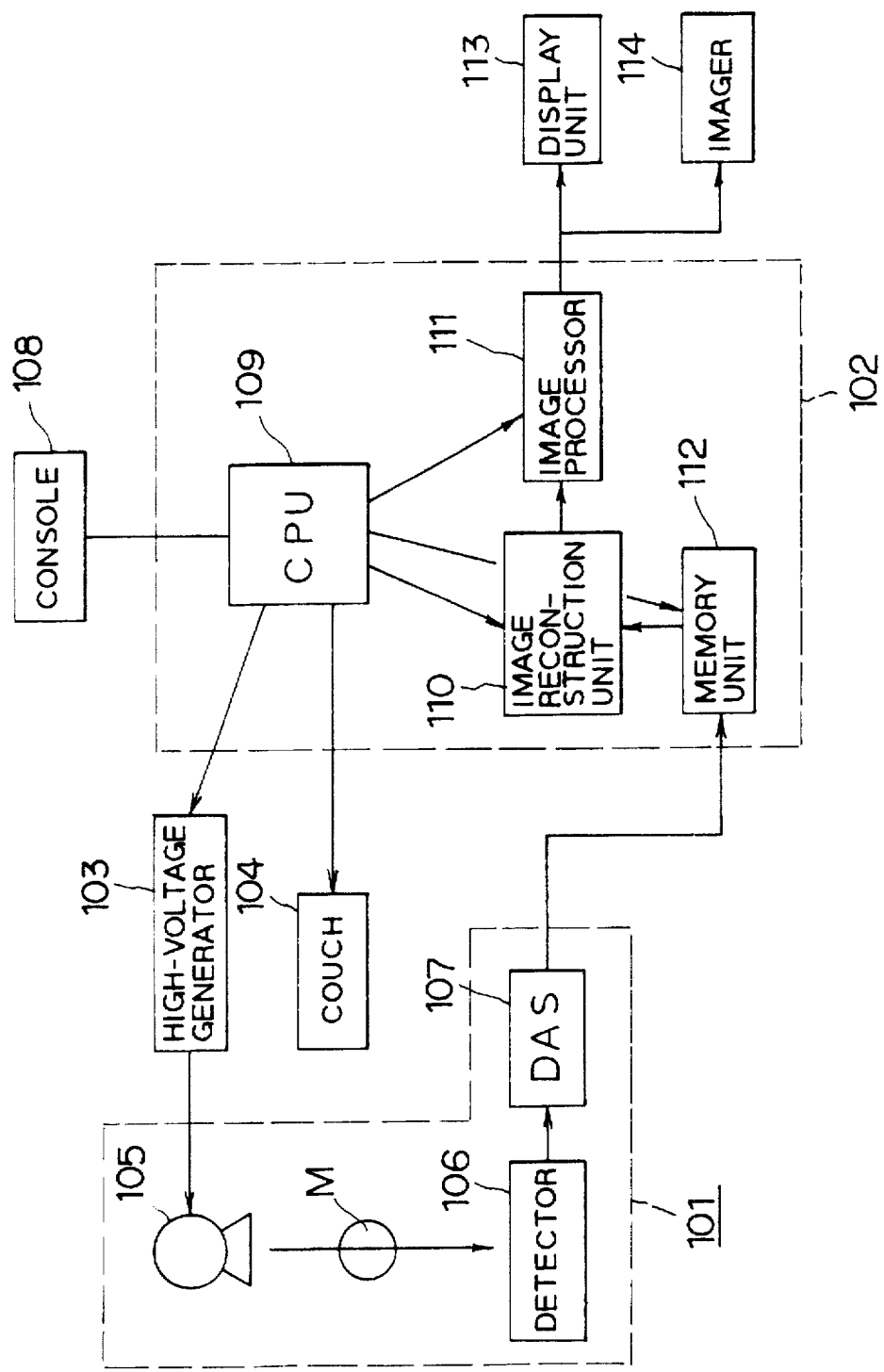
FIG. 1 is a block diagram showing a conventional X-ray CT scanner.
Figure 2:
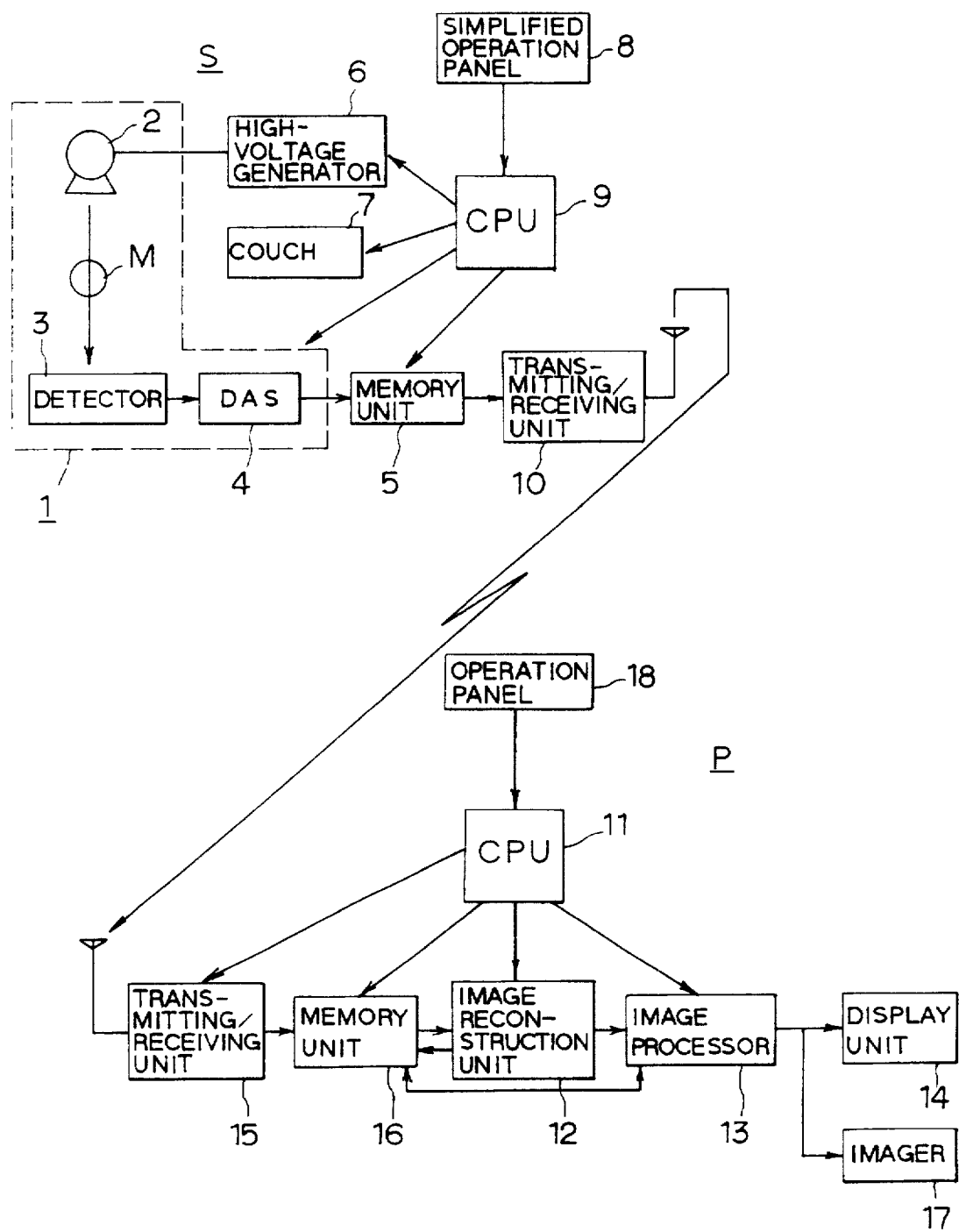
FIG. 2 is a block diagram showing an X-ray CT system in accordance with a first embodiment of the present invention.
Figure 3:
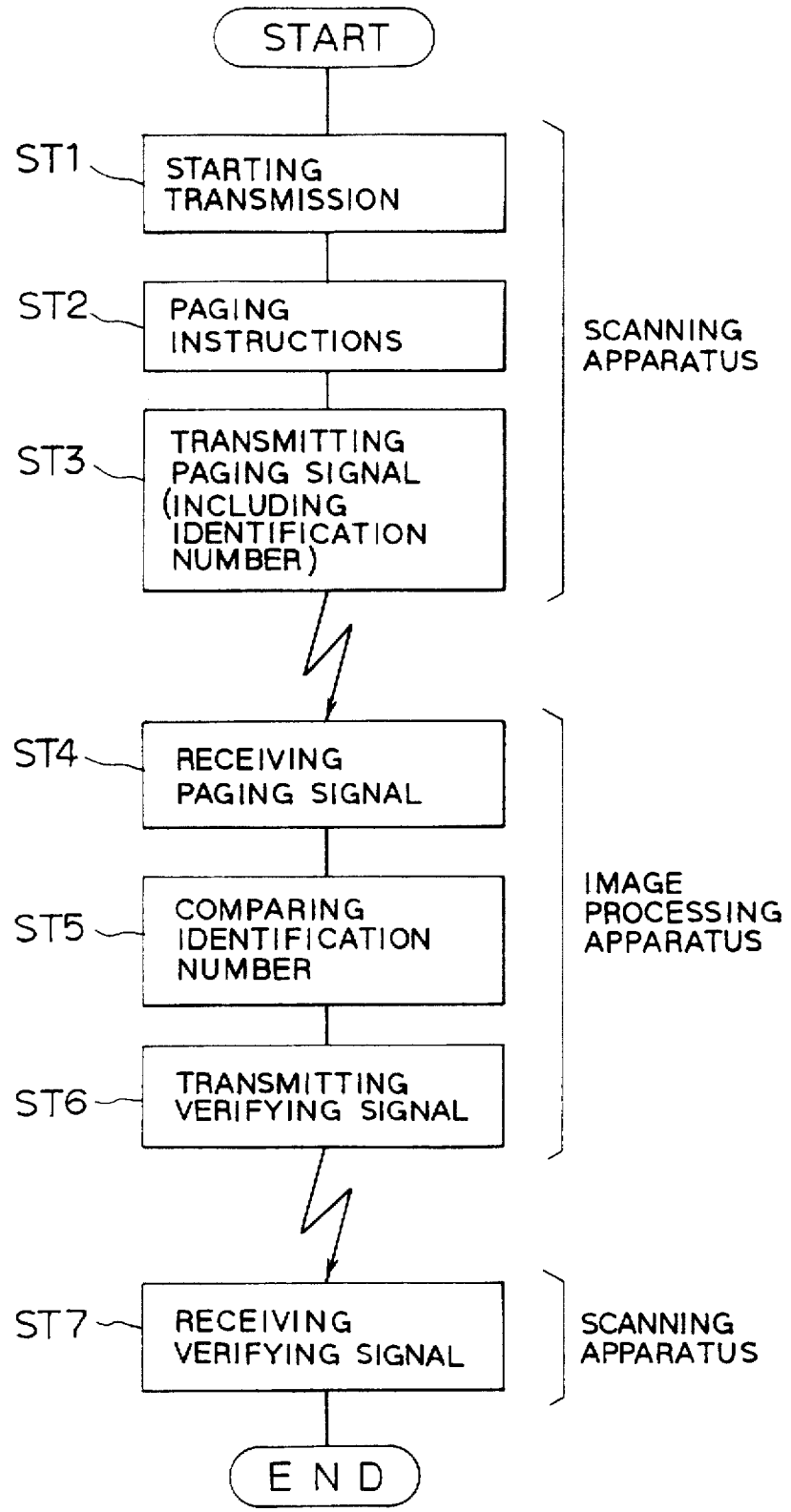
FIG. 3 is a flowchart showing a process for verifying a data transmission and reception at the side of a scanning unit and at the side of an image processor in accordance with a first embodiment of the present invention.

Referring to FIGS. 2 and 3, explained in an X-ray CT system in accordance with a first example of the present invention. S scanning apparatus (i.e. image data detecting apparatus) X included in the X-ray CT system of FIG. 2 has a scanner body (gantry) 1. The gantry 1 is furnished with an X-ray tube 2, a detector 3 and a data acquisition system (DAS) 4. Connected to an output side of the DAS 4 are a memory unit 5 and a transmitting/receiving unit 10 in sequence. The detector 3 detects X rays passing through the patient M and outputs an X-ray detection signal. The DAS 4 converts the X-ray detection signal to a digital signal. The memory unit 5 stores the scanning condition, time of inspection, place of inspection, patient's data, projection data, etc. The transmitting/receiving unit 10 transmits and receives data by means of an electromagnetic wave.

The scanning apparatus S is further provided with a high-voltage generator 6, a couch 7, a simplified operation unit 8 and a CPU (Central Processing Unit) 9. The high-voltage generator 6 generates high voltage supplied to the X-ray tube 2. The couch 7 moves having a patient M thereon. The simplified operation unit 8 is a handy operation panel to operate the scanning apparatus S. The CPU 9 generates control signals to control the scanning apparatus S.

Next, how the scanning apparatus S works will be explained. The patient M lying on the couch 7 is moved to the scanning position. Then, an operator inputs the patient's data, scanning condition, time of inspection and place of inspection to the simplified operation panel 8. The CPU 9 transmits these data to the memory unit 5 and has it store them. After the storage is completed, the CPU 9 transmits a scan starting signal to each unit. In this case, it is possible for the CPU 9 to transmit those data during scanning.

When the CPU 9 outputs the scan starting signal, each unit works as follows. The high-voltage generator 6 generates high voltage and supplies it to the X-ray tube 2. The X-rays tube 2 generates X-ray based upon the high voltage from a high-voltage generator 6 and irradiates the patient M. The detector 3 detects X rays passing through the patient M and outputs an X-ray detection signal to the DAS 4. The DAS 4 converts the X-ray detection signal to the digital signal and transmits it to the memory unit 5. The memory unit 5 stores the digital signal outputted from the DAS 4. The X-ray tube 2 and the detector 3 cooperatively detect the X rays passing through the patient M, both rotating about the patient M by way of a rotation mechanism (not shown).

Next, how an image processing apparatus P is constituted will be explained. The image processing apparatus P shown in FIG. 2 has a transmitting/receiving unit 15 for transmitting and receiving data by means of an electric wave. The transmitting/receiving unit 15 is connected to a memory unit 16. The memory unit 16, formed by a hard disk, for example, stores the transmitted scanning condition, time and place of inspection, patient's data, projection data, reconstructed data, processed image data, etc. Connected to the memory unit 16 are an image reconstruction unit 12 and an image processor 13 in sequence and in parallel. A CPU 11 controls each unit of the image processing apparatus P. An operation part 18 includes a panel to perform various operations for the image processing apparatus P.

The image reconstructs unit 12 reconstitutes an image from projection data and transmits the image reconstructed to the image processor 13 and if necessary, to the memory unit 16 for their storage. The image processor 13 performs image processings such as the enlarging, ROI (Region Of Interest) processing (i.e. reduction), etc. to the image reconstructed by the image reconstruction unit 12 and transmits the processed image to a display unit 14 and an imager 17 and if necessary, to the memory unit 16 for their storage. The display unit 14 displays an image transmitted from the image processor 13. The imager 17 records in a film an image transmitted through the image processor 13.

Next, how the image processing apparatus P works will be explained. The image reconstruction unit 12 reconstructs an image of the patient M based on the projection data stored in the memory unit 16 and transmits such image reconstructed to the image processor 13. The image processor 13 performs image processings based upon the operation information inputted to the operation panel 18 and transmitted through the CPU 11. The image processor 13 also transmits the processed image to the display unit 14 which is to display this image.

In this way the image reconstructed from the projection data obtained in the scanning unit S can be displayed in the display unit 14. Any images displayed in the display unit 14 may be recorded in the imager 17 by operating the operation part 18.

Next, referring to FIG. 3, provided is how the data is transmitted between the scanning apparatus S and the image processing apparatus.

In the first place it is requested to operate the simplified operation panel 8 and make the transmitting/receiving unit 15 be in a reception awaiting state. Then an operator operates the simplified operation panel 8 and instructs to start the data transmission (step 1). When the CPU 9 receives a signal to start the data transmission, it instructs the transmitting/receiving unit to transmit a paging signal (step 2). Having received the instructions from the CPU 9, the transmitting/receiving unit 10 transmits the paging signal including a unit identification number of the scanning apparatus S (step 3). When the transmitting/receiving unit 15 receives this paging signal (step 4), it compares the unit identification number included in this paging signal with a previously sorted unit identification number (step 5). If both unit identification numbers coincide with each other, the transmitting/receiving unit 15 transmits a reception verifying signal notifying the reception of the paging signal (step 6). When the transmitting/receiving unit 10 receives the reception verifying signal, it transmits to the CPU 9 a signal notifying the reception of this reception verifying signal (step 7). A circuit for transmitting the data is so verified.

Having verified the reception of the reception verifying signal, the CPU 9 instructs to transmit to the transmitting/receiving unit 10 the data on the unit identification number and other reconstruction data of the scanning unit S (the number of channels of the X-ray detector, the rotation radius of the X-ray detector, etc.). The transmitting/receiving unit 10 transmits these data as instructed. After the transmission of these data is completed, the CPU 9 instructs the memory unit 5 and the transmitting/receiving unit 10 to transmit the stored data. When the transmitting/receiving unit 10 receives such instructions from the CPU 9, it reads out from the memory unit 5 and transmits the stored data such as the scanning condition, patient's data, time of inspection, place of inspection, projection data, etc. When the stored data are totally read out, the CPU 9 instructs the transmitting/receiving unit 10 to finish the transmission. Having received the instructions, the transmitting/receiving unit 10 transmits a signal of transmission completion.

As the transmitting/receiving unit 15 receives the stored data such as the scanning condition, patient's data, time of inspection, place of inspection, projection data, etc., it transmits them to the memory unit 16 for storage. The data transmission is carried out in this manner. To verify the secure reception of the transmitted data a check mechanism may be arranged.

With this constitution the measuring of the X-ray projection data can be carried out with the scanning apparatus S that is the only apparatus set in a place of inspection. Consequently, such scanning apparatus S may be loaded in a bus and preferably applied to group inspection. Further, with the scanning apparatus loaded in an ambulance it is possible to transmit the data measured in the ambulance to an image processing section of a hospital and to diagnose a patient even before he or she arrives at the hospital.

As a variation of the aforementioned first example, a plurality of scanning apparatus S . . . S may be arranged for a single image processing apparatus P using the identification numbers for identifying a desired pair of one of the scanning apparatus S and the image processing apparatus P.

Figure 4:
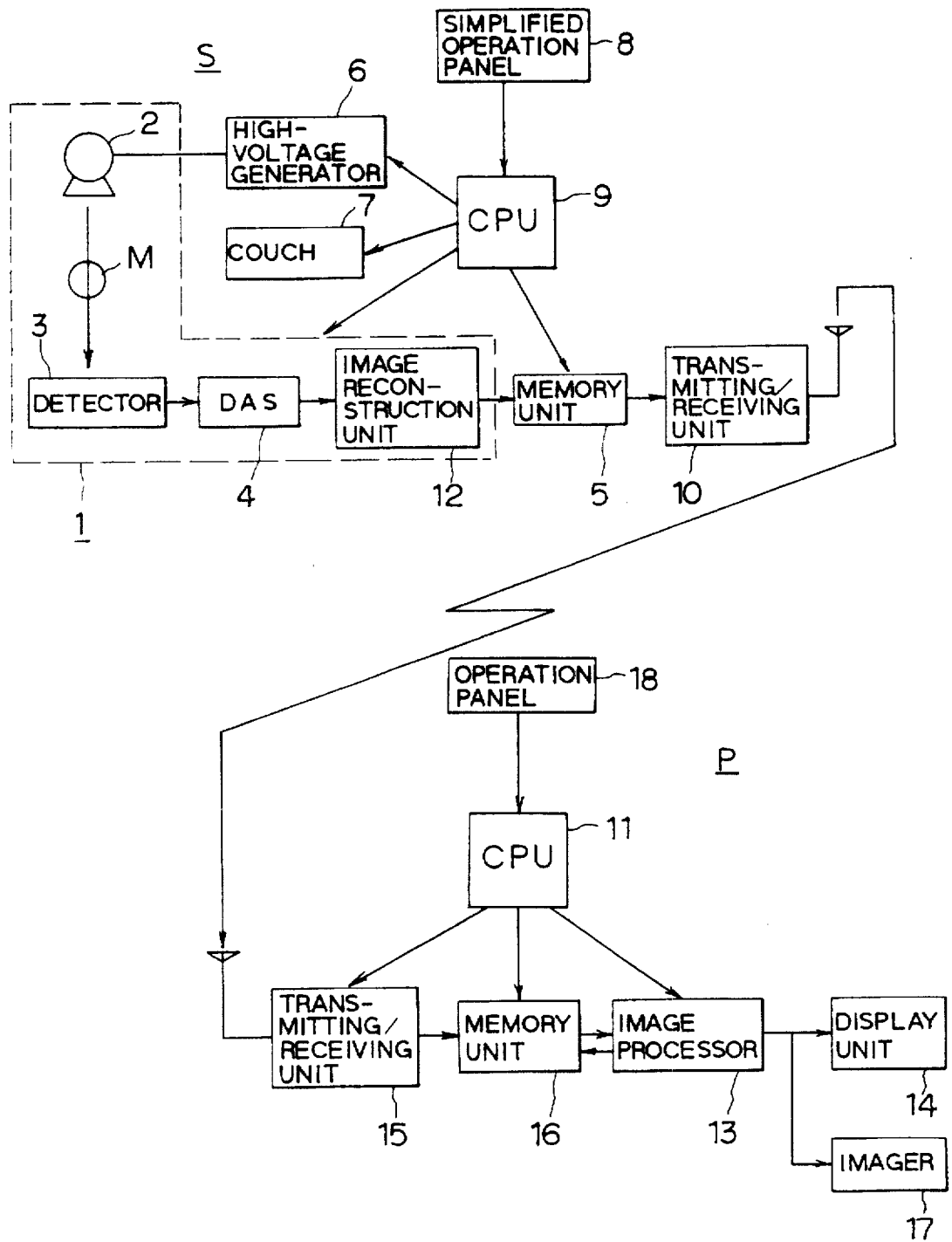
FIG. 4 is a block diagram showing an X-ray CT system in accordance with a second embodiment of the present invention.

Referring to FIG. 4, explained is an X-ray CT system in accordance with a second example of the present invention. In this X-ray CT system the image reconstruction unit 12 is disposed at the side of the scanning apparatus S. To begin with, each unit or element of this X-ray CT system and the relationships therebetween will be explained hereinbelow.

The explanations are left out for the same units or elements as those described in the first example.

The image reconstruction unit 12 that reconstructs the image from the X-ray projection data is arranged between the DAS 4 and the memory unit 5. The analog projection data detected by the detector 3 is converted to a digital projection data by the DAS 4 and transmitted to the image reconstruction unit 12. The image reconstruction unit 12 reconstructs the image from these digital projection data and transmits the image reconstructed to the memory unit 5 which is to store this image.

Next, as performed in the first example, the communication is executed between the transmitting/receiving unit 10 at the side of the scanning unit S and the transmitting/receiving unit 15 a the side of the image processing apparatus P, whereby the data stored in the memory unit 5 is transmitted to the memory unit 16. That is, the image is stored in the memory unit 16. Based upon the instructions through the operation panel 18, the image processor 13 performs various image processings to the image stored in the memory unit 16, converts such processed image to a video signal and transmits such signal to the display unit 14. The display unit 14 displays that video signal as an image.

Any image displayed on the display unit 14 may be recorded in the imager 17 by instruction through the operation panel 18. In this X-ray CT system the X-ray projection data can be measured by the scanning apparatus S that is the only apparatus set in a place of inspection. Thus, this scanning apparatus S becomes excellent in portability.

Figure 5:
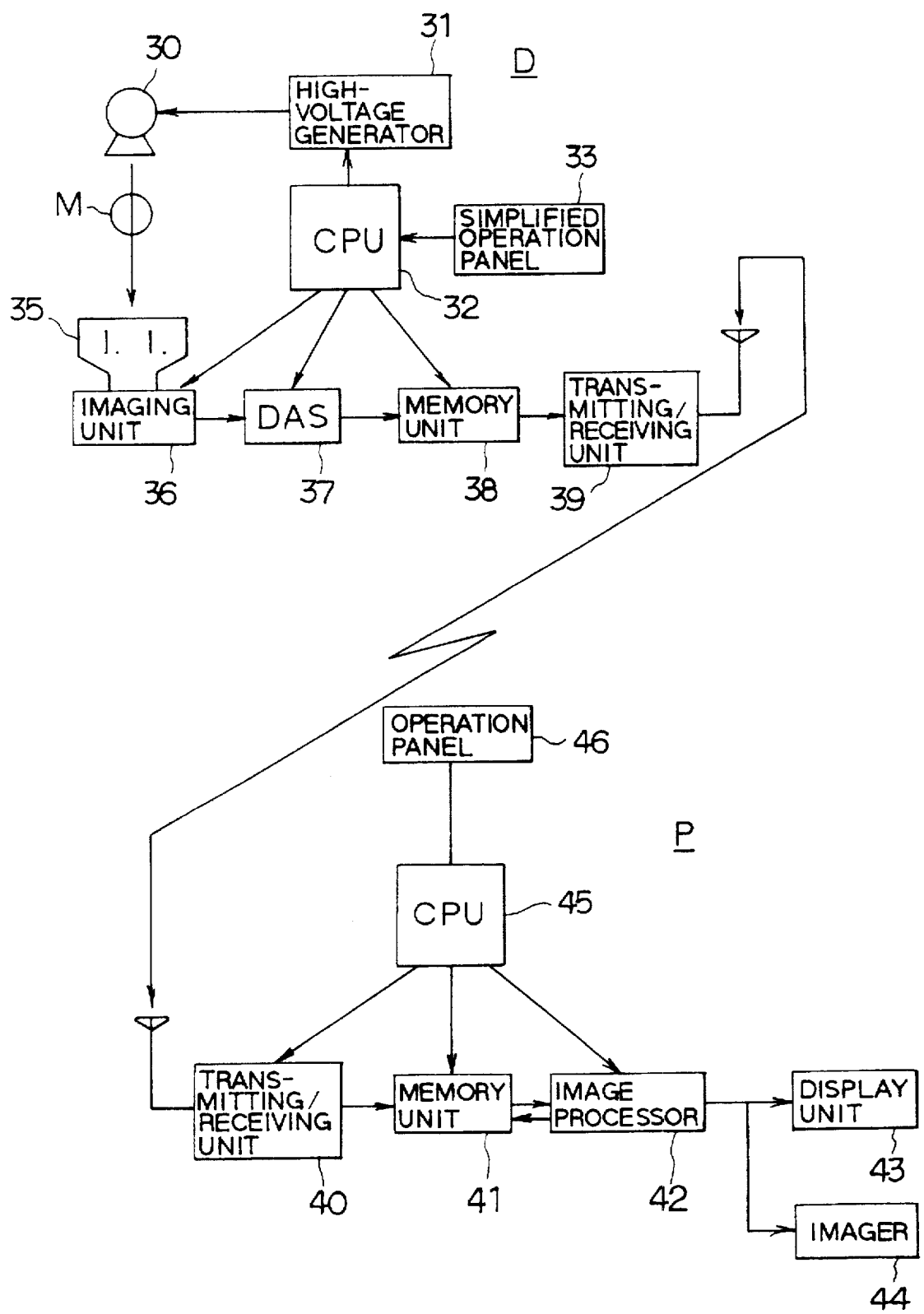
FIG. 5 is a block diagram showing an X-ray diagnostic system in accordance with a third embodiment of the present invention.

Referring to FIG. 5, explained is an X-ray diagnostic system in accordance with a third example of the present invention. A high-voltage generator 31 generates high voltage supplied to an X-ray tube 30. A couch (not shown) has a patient M lying thereon. An image intensifier 35 converts to an optical image X rays passing through the patient M. An imaging unit 36 converts to an analog image signal the optical image converted by the image intensifier 35. The DAS 37 converts to a digital signal the analog image signal outputted from the imaging unit 36. A transmitting/receiving unit 39 transmits and receives data by means of an electromagnetic wave. A simplified operation unit 33 is a handy operation panel to operate the scanning apparatus S. A CPU 32 generates control signals to control the scanning apparatus S.

Then, how the imaging unit D works will be explained. An operation inputs the patient's data together with a scanning condition and instructs to start the imaging. The CPU 32 has the memory unit 38 store the scanning condition, the patient's data, time and place of inspection as well as the image data. After these data have been stored, the CPU 32 transmits to each unit a signal to start the imaging.

When the CPU 32 outputs the signal to start the imaging, each unit works as follows. The high-voltage generator 31 generates high voltage and supplies it to the X-ray tube 30. The X-ray tube 30 generates X rays using the high voltage from the high-voltage generator 31 and irradiates the patient M. The image intensifier 35 converts to an optical image X rays passing through the patient M. The imaging unit 36 converts to an analog image signal the optical image converted by the image intensifier 35. The DAS 37 converts this image signal to a digital signal and transmits it the memory unit 38. The memory unit stores the digital signal from the DAS 37.

Next, as performed in the first example, the data stored in the memory unit 38 are transmitted to a transmitting/receiving unit 40 at the side of the image processing apparatus P.

In the image processing apparatus P shown in FIG. 5, a memory unit 41 stores the signal received by the transmitting/receiving unit 40. An image processor 42 performs the image processings such as enlarging, reducing, ROI processing, etc. to the image stored in the memory unit 41. A display unit 43 displays the image sent through the image processor 42. A CPU 45 controls each unit of the image processing apparatus P. An operation panel 46 is a panel to perform various kinds of operations for the image processing apparatus P. An imager 44 is a device to record the image sent through the image processor 42 in the form of film.

Next, explained is how the image processing apparatus P works. The way the data are received is left out since it is the same as that described in the first example.

Stored in the memory unit 41 are the image data output by the imaging unit 36. The image processor 42 reads out the image stored in the memory unit 41 and performs to such an image various kinds of image processing. The image processor 42 also converts the processed image to a video signal and transmits it to the display unit 43. The display unit 43 displays this video signal as an image. Displayed in this way is the image that is constructed from the projection data determined by the imaging unit D. In addition, any image can be recorded in the imager 44 by manipulation through the operation panel.

With this X-ray diagnostic apparatus, only setting the imaging unit D in a desired place is enough to obtain an X-ray projection image. Hence, there will be no need to place so many units in a single place, thereby making it easy to transport and/or set the units there. The imaging unit D may be loaded to a shooting car as suggested in the first example.

Further, since the imaging unit D can be manufactured relatively compact, making it movable in a hospital enables an X-ray projection image to be taken in each sickroom. In this case, the image can be transmitted through a communication circuit such as a LAN (Local Area Network) using an optical fiber, concentric cable, etc.

Figure 6:
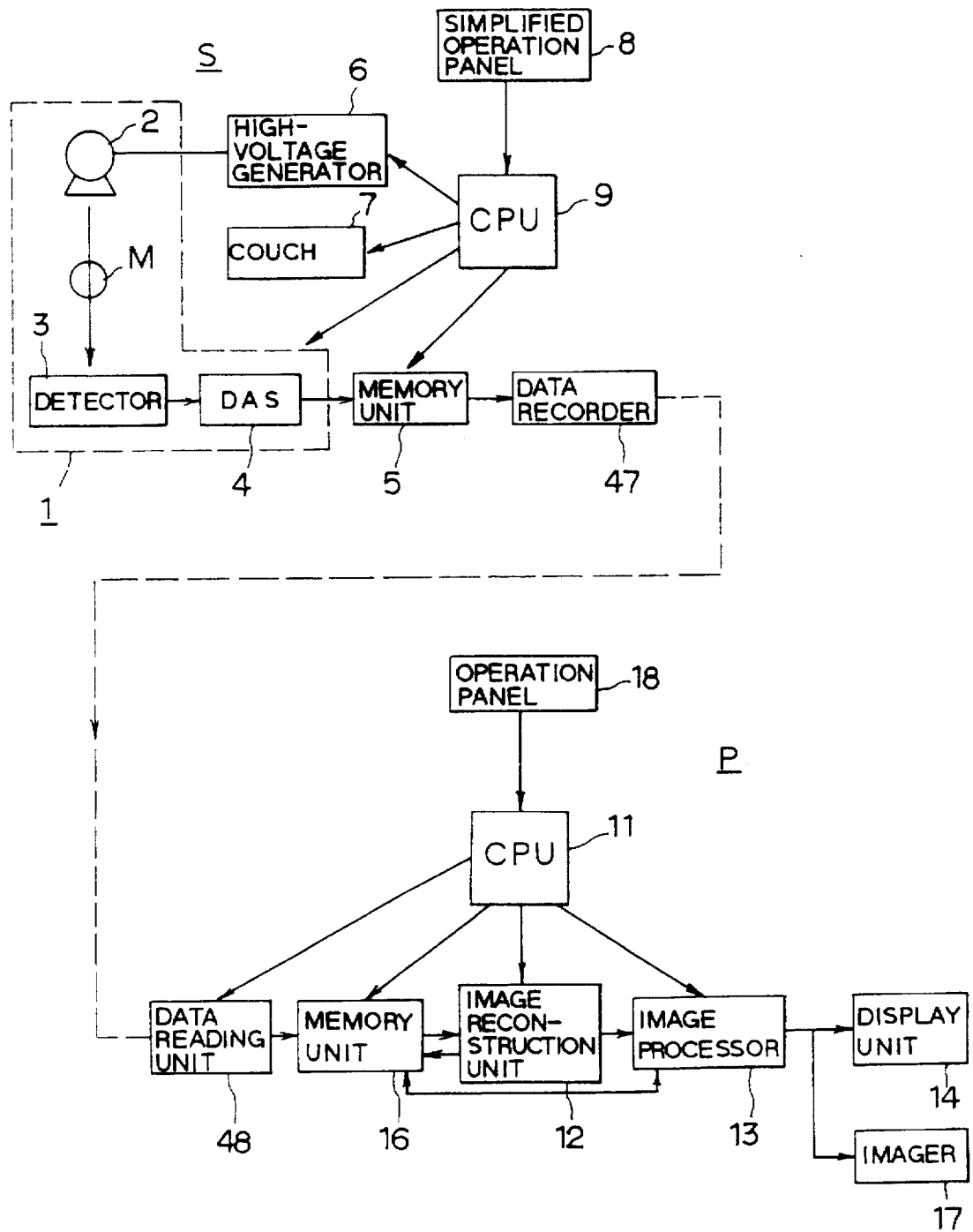
FIG. 6 is a block diagram showing an X-ray CT system in accordance with a fourth embodiment of the present invention.

Referring to FIG. 6, explained in a fourth example of the present invention. The explanation will be omitted for the same units as those described in the first example. In the present example the information is conveyed with a record medium in place of the communication apparatus.

An X-ray CT system of the present example has a data recorder 47 and a data reading unit 48 instead of the transmitting/receiving unit 10 and 15, respectively, shown in FIG. 2. The data recorder 47 records in a magnetic optical disk (i.e., forming a portable record medium of the present invention) the data such as an identification number of the scanning apparatus S sent from the CPU 9, unit configuration of the scanning apparatus S, the scanning condition stored in the memory unit 5, the patient's data, time and place of inspection, projection data, etc. The data reading unit 48 reads out the data stored in the magnetic optical disk and sends them to the memory unit 16 for storage. The image reconstruction unit 12 reconstructs the image based on the data stored in the memory unit 16 and sends it to the image processor 13. The image processor 13 performs various kinds of image processings to the tomography reconstructed by the image reconstruction unit 12 and sends such a processed image to the display unit 14 for displaying it.

With this X-ray CT system, since the data are conveyed with a record medium having them recorded thereon, this system can be employed even in a place where an electromagnetic wave tends to be obstructed and the communication is hard to make. Such a method using a record medium may be employed in the second or third example as well.

Figure 7:
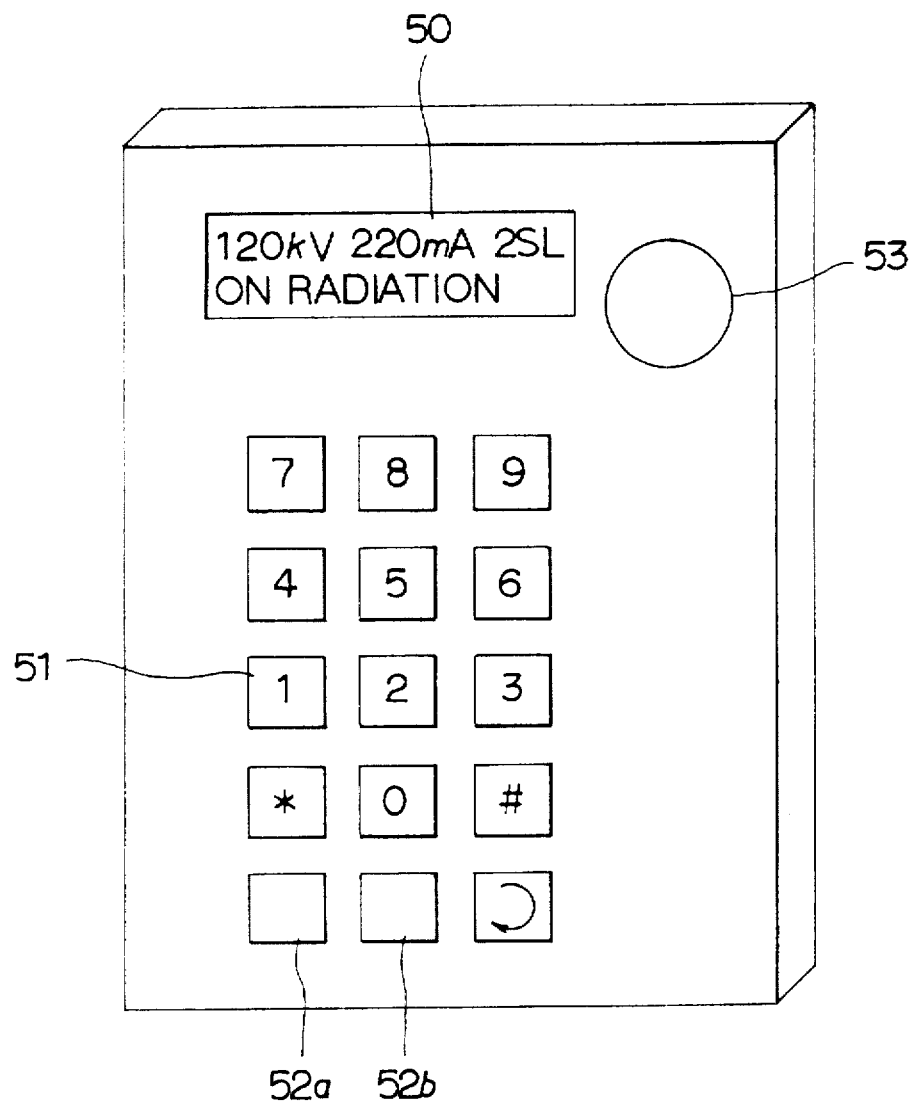
FIG. 7 is a perspective view showing a simplified operation panel in accordance with a fifth embodiment of the present invention.

Referring to FIG. 7, explained in a fifth example of the present invention. The fifth example relates to a scanning portion, particularly a simplified operation panel in an imaging part.

FIG. 7 is a perspective view of the simplified operation panel. The simplified operation panel comprises a simplified display portion 50, input keys 51, a scan start key 52, and an emergency stop switch 53. This simplified operation panel is of size of about 18 cm (height) × 12 cm (width). The input keys 51 include 13 push buttons composed of "10" keys, a "#" key, an "*" key and an "enter" key. Those input keys are located under the simplified display portion 50. The scan start key includes two push buttons. The emergency stop switch 53 is a relatively large push button switch so as to operate quickly in emergency. This emergency stop switch is located at the right of the simplified display portion 50.

Next, explained is how each portion of the simplified operation panel works. An operation inputs a shortened number representing the predetermined scanning conditions. The inputted shortened number is sent to the CPU which is connected to the simplified operation panel. The CPU sets the scanning conditions (the strength of X-ray, scanning rate, scanning mode, etc.) corresponding to the shortened number and, at the same time, sends to the simplified display portion 50 the data of the shortened number and the scanning conditions for displaying them. Suppose inputting "* 1 enter", then this inputted data is sent to the CPU connected to the simplified operation panel. The CPU sets the scanning conditions for head diagnosis. On the other hand, when inputting "* 2 enter", then set are the scanning conditions for abdominal diagnosis.

Then, the operator inputs the patient's data through the input keys 51. The patient's data includes a numerical identification data such as a sorting number, etc. Suppose inputting "# 1 2 3 enter", then "123" is stored as patient's data.

To instruct the start of scan, one pushes both the scan start keys 52a and 52b simultaneously. The reason why two buttons are given as a scan start key is to prevent the operator from erroneously instructing the start of scan.

In case that an emergency occurs during the scan, one is able to stop the scan by pushing the emergency stop button 53.

With this simplified operation panel, the operation part of the scanning apparatus or the imaging unit can be compact. Alphabet keys or Japanese letter keys may be employed for inputting a patient's identification data instead of numerical keys ("10" keys) used in the present example. Moreover, a bar-code reader may be provided in order to smooth the inputting of the scanning conditions or the patient's data.

The present invention is in no way limited to the foregoing examples. Those skilled in the art may make various modifications within the spirit and the scope of the present invention. For instance, when transmitting data, possible is compressing the data with a data compressing unit. Further, a plurality of the scanning apparatus or the imaging units can be set for a sole image processing apparatus.

This idea disclosed herein is applicable to an MRI apparatus and/or a SPECT apparatus other than an X-ray CT apparatus and an X-ray diagnostic apparatus. Further, it may be possible to operatively connect to one image processing apparatus different kinds of diagnostic apparatus such as an X-ray CT apparatus, an X-ray diagnostic apparatus, an MRI apparatus, etc.

Moreover, an electromagnetic wave described in the foregoing examples or an optical fiber and/or a concentric cable suggested therein may be replaced with other means of communication, e.g. a geostationary satellite and/or a telephone circuit. Also, it may be possible to receive the data transmitted only from the scanner having the same identification number as the one stored previously at the side of the image processing apparatus.

What is claimed is:

1. An X-Ray CT scanner system comprising:

- a plurality of image data detecting apparatus, each apparatus having a pre-given, individual identification code to distinguish each image data detecting apparatus from the other image data detecting apparatus; and
- an image processor placed separately from and operatively connected to each of the plurality of image data detecting apparatus through a communication medium, wherein each of the plurality of image data detecting apparatus comprises:

- an X-ray generating means for generating X rays toward an object;
- an X-ray data acquisition system for detecting the X rays passing through the object and outputting X-ray projection data corresponding to the detected X rays, and
- an information transmitting means for transmitting through the communication medium to the image processor the pre-given identification code and information including the X-ray projection data; and wherein the image processor comprising:

- an inputting means for inputting the identification code and the information transmitted through the communication medium, the inputting means including means for verifying the identification code; and
- an image reconstruction means for reconstructing a tomography image based on the X-ray projection data.

2. The X-ray CT scanner system of claim 1 wherein said communication medium includes an electric wave.

3. The X-ray CT scanner system of claim 1 wherein said communication medium includes a telephone line.

4. The X-ray CT scanner system of claim 1 wherein said communication medium includes an information record medium.

5. The X-Ray CT scanner system of claim 1, wherein said information transmitting means comprises:

- means for transmitting the pre-given, individual identification code to the image processor through the communication medium;
- means for receiving a verifying signal from the image processing means through the communication medium; and
- means for transmitting the information including the X-ray projection data acquired by the X-ray data acquisition system to the image processor through the communication medium after the verifying signal is received by the receiving means; and wherein said verifying means comprises:

- means for receiving the pre-given, individual identification code transmitted through the communication medium by the identification code transmitting means;
- means for verifying the identification code received by the identification code receiving means; and
- means for transmitting to the information transmitting means for the verifying signal through the communication medium after verification of the pre-given, individual identification code of the image data detecting apparatus.

* * * * *

UNITED STATES PATENT AND TRADEMARK OFFICE
CERTIFICATE OF CORRECTION

PATENT NO. : 5,751,837
DATED : May 12, 1998
INVENTOR(S) : Watanabe et al.

It is certified that error appears in the above-identified patent and that said Letters Patent is hereby corrected as shown below:

Title Page, Item [54], in the Title, line 2, "SCANNER" should read --SCANNING--.

Title Page, Item [57], in the Abstract, line 4, "X-rays" should read --X rays--.

Claim 1, Column 9, line 10, "X-Ray" should read --X-ray--.

Claim 5, Column 10, line 8, "X-Ray" should read --X-ray--.

Claim 5, Column 10, line 31, before "the verifying", delete "for".

Signed and Sealed this

Twenty-fifth Day of May, 1999

Attest:

Q. TODD DICKINSON

Attesting Officer

Acting Commissioner of Patents and Trademarks